US012369829B2

(12) United States Patent
Myllykangas et al.

(10) Patent No.: US 12,369,829 B2
(45) Date of Patent: Jul. 29, 2025

(54) ELECTRIC APPARATUS AND ITS MANUFACTURING METHOD

(71) Applicant: BITTIUM BIOSIGNALS OY, Kuopio (FI)

(72) Inventors: Juha Myllykangas, Kuopio (FI); Arto Nikula, Kuopio (FI)

(73) Assignee: Bittium Biosignals Oy, Kuopio (FI)

( * ) Notice: Subject to any disclaimer, the term of this patent is extended or adjusted under 35 U.S.C. 154(b) by 742 days.

(21) Appl. No.: 17/645,818

(22) Filed: Dec. 23, 2021

(65) Prior Publication Data

US 2023/0200705 A1 Jun. 29, 2023

(51) Int. Cl.
| | |
|---|---|
| *A61B 5/29* | (2021.01) |
| *A61B 5/28* | (2021.01) |
| *A61B 5/291* | (2021.01) |
| *A61B 5/318* | (2021.01) |
| *A61B 5/36* | (2021.01) |
| *A61B 5/369* | (2021.01) |

(52) U.S. Cl.
CPC ............... *A61B 5/291* (2021.01); *A61B 5/28* (2021.01); *A61B 5/318* (2021.01); *A61B 5/369* (2021.01)

(58) Field of Classification Search
CPC ......... A61B 5/291; A61B 5/369; A61B 5/318; A61B 5/28; A61B 5/321; A61B 5/33; A61B 5/25
See application file for complete search history.

(56) References Cited

U.S. PATENT DOCUMENTS

| 3,982,529 | A  | * | 9/1976  | Sato ........................ A61B 5/25 600/397 |
| 11,116,448 | B1 | * | 9/2021  | Trapero Martin ... A61B 5/0816 |
| 11,266,476 | B1 | * | 3/2022  | Willis ..................... A61B 5/256 |
| 2017/0055896 | A1 | * | 3/2017  | Al-Ali ..................... A61B 5/1116 |
| 2019/0334304 | A1 | * | 10/2019 | Myllykangas ......... H01R 33/97 |
| 2020/0221968 | A1 | * | 7/2020  | Gumiero ................ A61B 5/282 |

OTHER PUBLICATIONS

U.S. Appl. No. 17/432,724, Myllykangas et al., filed Jun. 9, 2021.

* cited by examiner

*Primary Examiner* — Joanne M Rodden
*Assistant Examiner* — Alyssa M Pape
(74) *Attorney, Agent, or Firm* — Nixon & Vanderhye PC (57) ABSTRACT

An electric apparatus of a bio-signal measurement system comprising a front part and a back part. The front part comprises a compartment at a back side of the front part, the compartment housing the back part when inserted therein. The back part comprises an electric circuit conductors and an extension plate, which extends to the front part within the electric apparatus. The extension plate comprises first electric contacts of the electric circuit conductors, the first electric contacts residing within the front part when the back part is within the compartment, the first electric contacts acting as counter-electrodes or electrodes of a front flap of a disposable patch electrode structure. The electric apparatus receives the front flap of the disposable patch electrode structure into a volume of the front part for forming a contact between the first electric contacts and the electrodes of the front flap. At least one of the back part and the front part comprises resin holes, and the compartment contains resin received through the resin holes, the resin immobilizing the front part and the back part with respect to each other and attaching them together.

12 Claims, 5 Drawing Sheets

ELECTRIC APPARATUS AND ITS MANUFACTURING METHOD

FIELD

The invention relates to an electric apparatus and its manufacturing method.

BACKGROUND

An electronic device, which measures bio-signals such as ECG (ElectroCardioGram) and EEG (ElectroEncephaloGram), must be well contacted with the electrodes that are in contact with the body and mechanically reliably fixed to its support. Typically there is at least some electromechanical part for connecting and fixing the non-disposable bio-signal measurement device into the disposable single-use electrode part. An electromechanical connector is a both complicated and expensive part to manufacture and assemble on the disposable patch electrode. Because the patch electrode will be disposed after only a single use, also electromechanical connector is discarded with the patch electrode.

BRIEF DESCRIPTION

The present invention seeks to provide an improvement in the measurements.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

The term "about" means that quantities or any numeric values are not exact and typically need not be exact. The reason may be tolerance, resolution, measurement error, rounding off or the like, or a fact that the feature of the solution in this document only requires that the quantity or numeric value is approximately that large. A certain tolerance is always included in real life quantities and numeric values.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Examples of an electric apparatus 30 are explained below with FIGS. 1 to 8.

Figure 1:
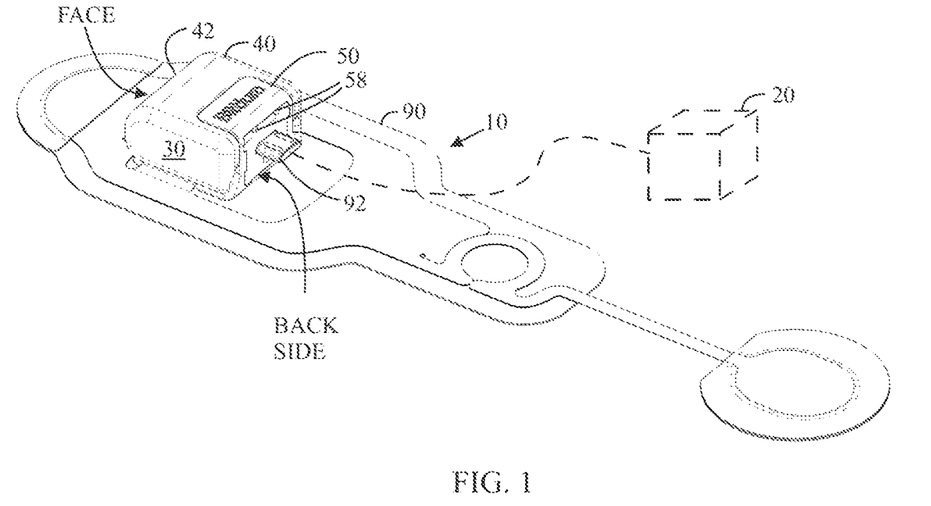
FIG. 1 illustrates an example of an electric apparatus that is in mechanical and electrical contact with a patch electrode structure.

FIG. 1 illustrates an example of an electric apparatus 30 that is in mechanical and electrical contact with a patch electrode structure 10. The patch electrode structure 10 is a piece of sheet that may be narrow like a band or broad like a wider planar surface and it is often fairly thin. The dimensions of the patch electrode structure 10 may resemble those of sheet of plastic, paper, board or cloth. The patch electrode structure 10 is configured to be attached to skin of a mammal such as a human being for a bio-signal measurement. The bio-signal may be related to body movement, body temperature, heart rate variability, electrocardiogram, electromyogram, electroencephalogram or the like for example. During a measurement, the patch electrode structure 10 feeds directly or indirectly electrical bio-signals to a non-disposable bio-signal device that is separate from the patch electrode structure 10. The disposable patch electrode structure 10 may have a PET-layer.

In an embodiment, the electric apparatus 30 may comprise the non-disposable bio-signal device 20. In an embodiment, the electric apparatus 30 may be a wired connector between the patch electrode structure 10 and the bio-signal device 20 (shown with dashed lines in FIG. 1). The electric apparatus 30 may comprise a back side connector 92, which may be a universal series bus (USB) connector, for example.

Figure 2:
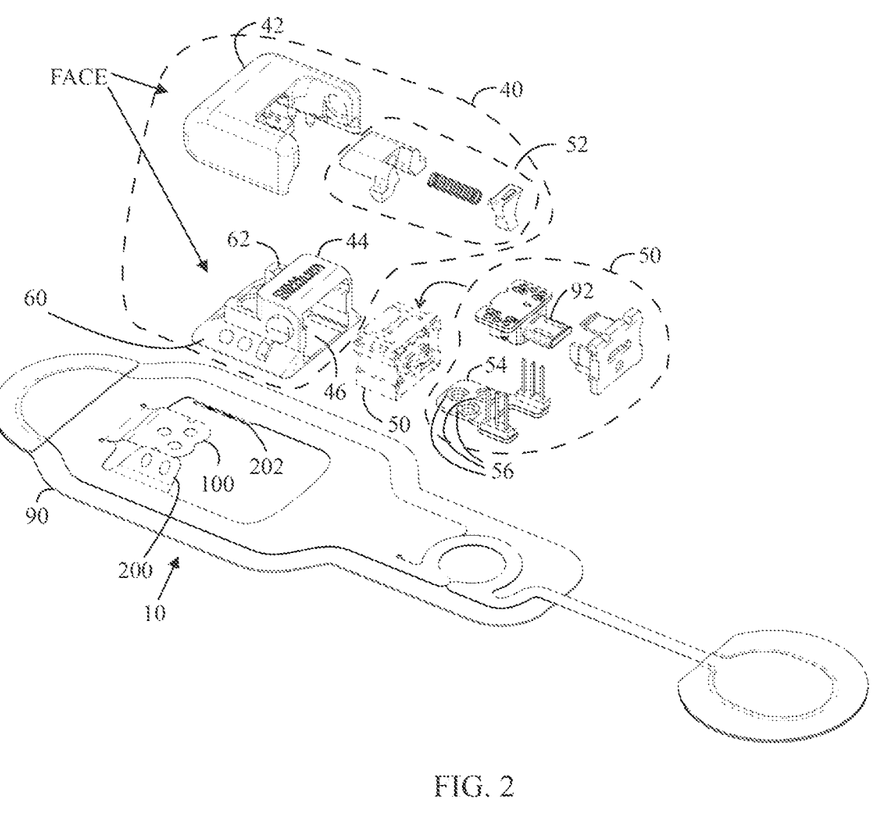
FIG. 2 illustrates an example of an exploded view drawing of the non-disposable electric apparatus.

FIG. 2 illustrates an example of an exploded view drawing of the non-disposable electric apparatus 30 of the bio-signal measurement system. The electric apparatus 30 comprises a front part 40 and a back part 50. The front part 40 comprises a lid 42 and a frame part 44. The frame part 44 and the lid 42 together comprise or are mechanically connected with a quick locking mechanism 52 for locking the lid 42 in the closed position with respect to the frame part 44. The lid 42 is configured to open at a face of the front part 40 for forming an opening 70 (see FIG. 8) to the front part 40. The front part 40 comprises a compartment 46 at a back side of the front part 40. The compartment 46 is configured to house the back part 50 when the back part 50 is inserted therein. The compartment 46 is made to match with the back part 50 within tolerances.

The frame part 44 of the front part 40 may comprise a wall 48 at an end of the compartment 46 within the front part 40. The wall 48 comprises an aperture 32. The aperture 32 may be rectangular, for example.

Figure 5:
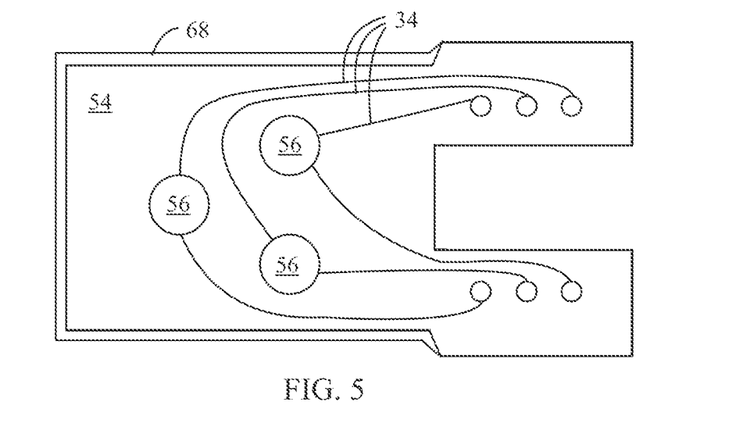
FIG. 5 illustrates an example of an extension plate.

As illustrated in FIG. 5, the back part 50 comprises an electric circuit conductors 34 and an extension plate 54, which is configured to extend through the aperture 32 to the front part 40 when the back part 50 is inserted in the compartment 46. Shapes of the aperture 32 and the extension plate 54 are matched together for making the aperture 32 with the extension plate 54 resin proof.

The extension plate 54 comprises first electric contacts 56 of the electric circuit conductors 34 (see FIG. 5). The first electric contacts 56 being configured to reside within the front part 40 when the extension plate 54 has penetrated the aperture 32 while the back part 50 is within the compartment 46, and the first electric contacts 56 acting as counter-electrodes for electrodes 110 of a front flap 100 of a disposable patch electrode structure 10.

The electric apparatus 30 is configured to slide on a main structure 90 of a disposable patch electrode structure 10 toward a front flap 100 of the patch electrode structure 10 with the face ahead, and receive the front flap 100 through the opening 70 of the lid 42 into a volume under the lid 42 for forming a contact between the first electric contacts 56 and the electrodes 110 of the front flap 100.

The lid 42 is configured to cause pressure between the first electric contacts 56 and the electrodes 110 of the front flap 100 while the lid 42 is closed.

At least one of the back part 50 and the front part 40 comprises resin holes 58. The compartment 46 contains resin received through the resin holes 58. The resin is configured immobilize the front part 40 and the back part 50 with respect to each other and attach them together while the wall 48 is configured to keep the volume under the lid 42 and the compartment 46 as separate departments and prevent the resin from entering the volume under the lid 42 during the manufacturing phase. The resin is curable and after it has hardened the front part 40 and the back part 50 cannot be separated from each other.

The resin may be a synthetic or natural polymer that may be used as an adhesive. The resin is used in the electric apparatus as a filler which also glues parts of the electric apparatus together in the back side. The resin may be thermoplastic, for example. The resin may be epoxy, silicon, 2k-glue, polyurethane or the like, for example.

In an embodiment, the front part 40 and the back part 50 together may comprise a non-openable instant interlocking structure 64 which attaches the front part 40 and the back part 50 together preventing them from moving with respect to each other.

Figure 3:
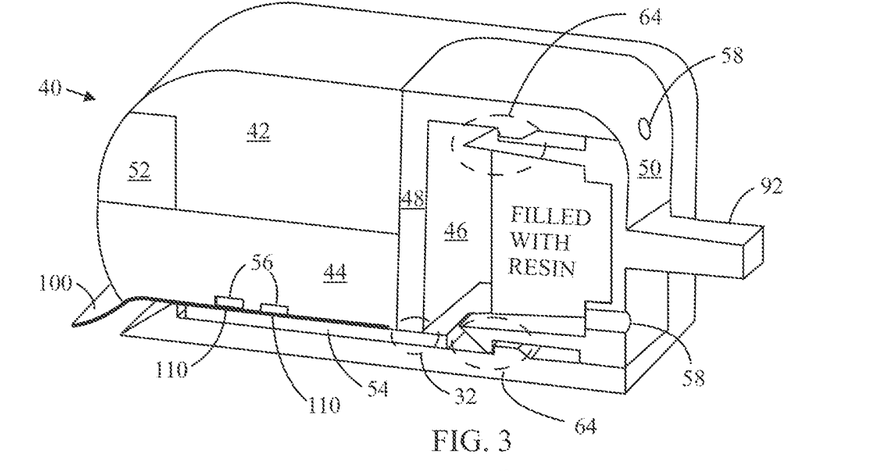
FIG. 3 illustrates an example of a cross section of the electric apparatus connected with a flap electrode system.

FIG. 3 illustrates an example of a cross section of the electric apparatus 10 with the front flap 200 inside the electric apparatus 10. The lid 42 causes pressure between the front flap 100 and the first electric contacts 56 while the lid 42 is closed for securing an efficient electric and mechanical contact between the electric apparatus and the disposable patch electrode structure 10.

In an embodiment an example of which is illustrated in FIG. 3, the opening 70 of the front part 40, the opening 70 being formed under the lid 42 when the lid 42 is raised, may also receive side flaps 200 of the disposable patch electrode structure 10 at both sides 60, 62 of electric apparatus. The lid 42 may then cause pressure between the sides 60, 62 and the side flaps 200 while the lid 42 is closed for securing an efficient mechanical contact between the electric apparatus and the disposable patch electrode structure 10.

Figure 4:
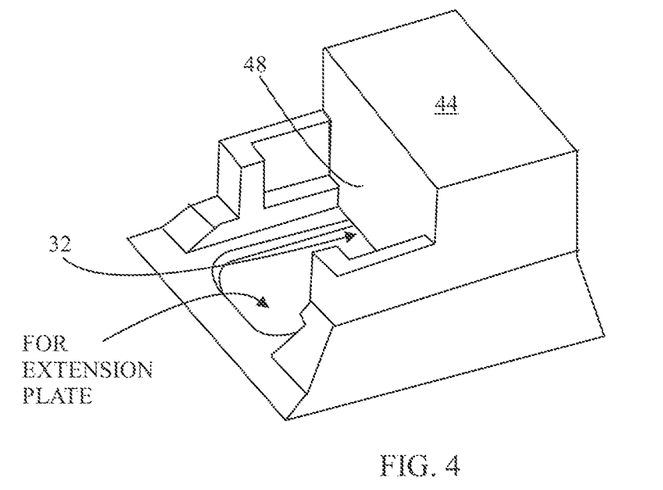
FIG. 4 illustrates an example of a frame part.

FIG. 4 illustrates an example of the frame part 44. When the back part 50 is inserted into the compartment 46, the extension plate 54 may extend through the aperture 32 to the front part 40. Shapes of the aperture 32 and the extension plate 54 are matched together for making the aperture 32 with the extension plate 54 resin proof.

The extension plate 54 comprises first electric contacts 56 of the electric circuit conductors 34 (see FIG. 5). The first electric contacts 56 being configured to reside within the front part 40 when the extension plate 54 has penetrated the aperture 32 while the back part 50 is within the compartment 46, and the first electric contacts 56 acting as counter-electrodes for electrodes 110 of a front flap 100 of a disposable patch electrode structure 10.

FIG. 5 illustrates an example the extension plate 54, which comprises the first electric contacts 56 of the electric circuit conductors 34. FIG. 5 also illustrates an embodiment, where the frame part 44 has a clearance 68 along the length of the extension plate 54. However, at the wall 48 the clearance 68 is smaller because of a widening wedge shape of the extension plate 54. In this manner, the sides of the extension plate 54 and the frame part 44 are made to touch each other when the extension plate 54 is properly inserted within the compartment 46. When the extension plate 54 and the frame part 44 touch each other they close the clearing 68 and prevent the resin from entering the front part 40 through the aperture 32 of the wall 48.

Figure 6:
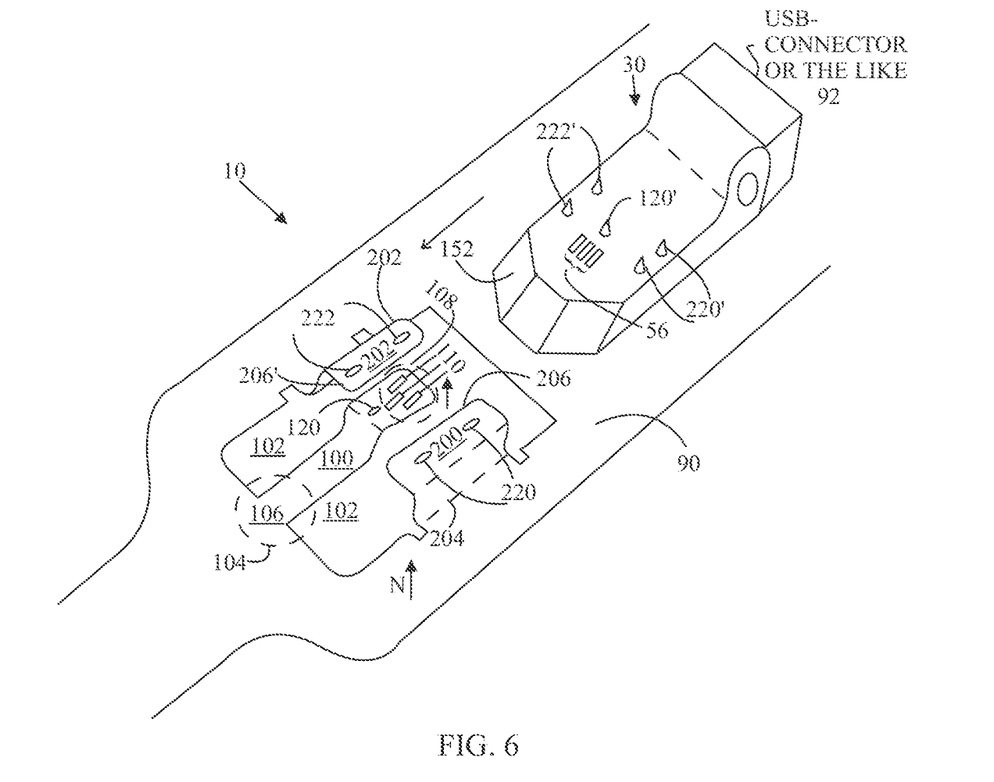
FIG. 6 illustrates an example of a disposable patch electrode structure that comprises a front flap and a main structure and the electric apparatus.

FIG. 6 illustrates the disposable patch electrode structure 10 and the electric apparatus with the lid 42 removed. The front flap 100 that is a similarly thin as the rest of the patch electrode structure 10 is separated from the main structure 90 by a non-enclosing front flap cut 102 that does not fully enclose or encircle an area of the patch electrode structure 10. The front flap 100 is attached and thus hinged at a rear side 104 with the main structure 90. Material of the front flap 100 thus forms a continuous materialistic connection 106 with the main structure 90 because their basic structure is the same or similar. The front flap 100 is thus integrated materialistically with the main structure 90.

The materialistic connection 106 of the continuous material between a rear section 104 of the front flap 100 at a non-enclosing side of the front flap cut 102 and the main structure 90 allows a tilt of the front flap 100 with respect to the main structure 90 in response to rise of a frontal section 108 of the front flap 100 with respect to the main structure 90. The frontal section 108 of the front flap 100 rises when tilted in a direction of a normal N of the main structure 90. The frontal section 108 is opposite to the rear section 104.

The front flap 100 is fully surrounded by the main structure 90 in a plane of the disposable patch electrode structure 10.

The front flap 100 comprises contact electrodes 110 at a frontal section 108 of the front flap 100. The contact electrodes 110 may be AgCl-printed electrodes, for example (AgCl means silver chloride). The contact electrodes 110 may be on one side of the front flap 100 and can be understood to be a "backside" of the front flap 100 although the contact electrodes 110 are drawn visible on the front flap 100 in FIG. 6. The contact electrodes 110 are on the same surface of the patch electrode structure 10 as measurement electrodes 112 that are configured to be touching the skin of a mammal during a bio-signal measurement. As can be seen in FIG. 6, the counter-electrodes 56 can contact with the contact electrodes 110 when the contact electrodes 110 are on the "backside" the front flap 100 i.e. on side that comes in contact with the counter-electrodes 56. The contact electrodes 110 are both connected with the measurement electrodes 112 of the main structure 90 through conductors via the materialistic connection 106 and configured to connect with counter-electrodes 56 of the electric apparatus 30 separate from the patch electrode structure 10. The counter-electrodes 56 may be flexible, spring-like curves of metal, for example.

Figure 7A:
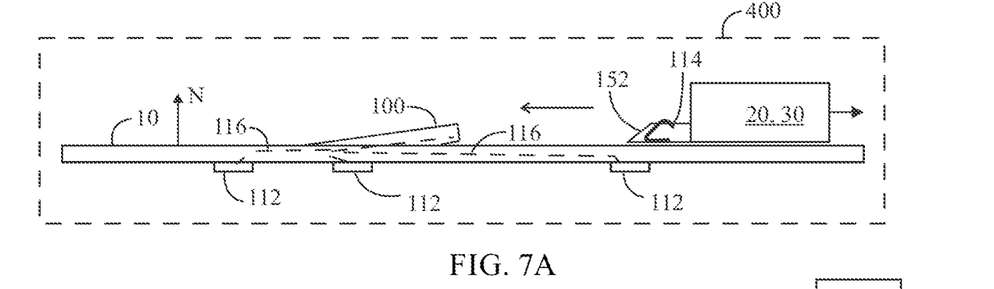
FIG. 7A to 7C illustrates an example of the disposable patch electrode structure a front flap of which is approached and connected with by the electric apparatus.
Figure 7B:
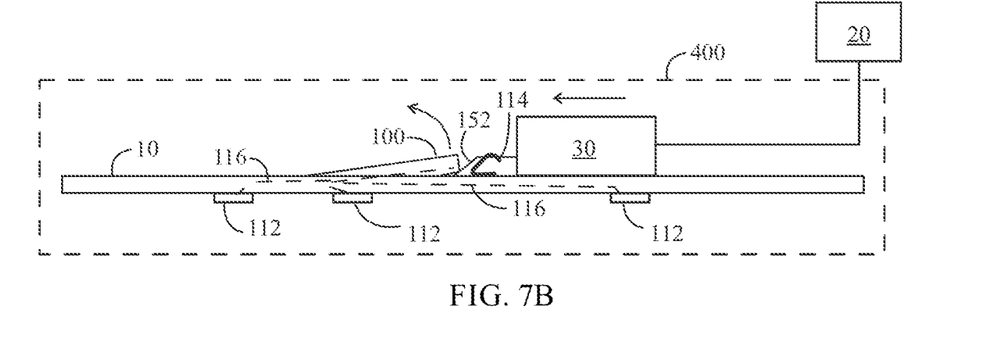
Figure 7C:
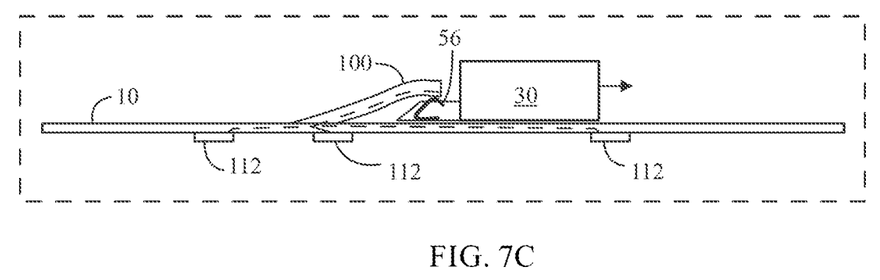

FIGS. 7A, 7B and 7C illustrate an example when the electric apparatus 30 is on the patch electrode structure 10. In FIG. 7A, the electric apparatus 30 is at a distance from the front flap 100. In FIG. 7B, the electric apparatus 30 is in contact with the front flap 100 and about to rise the front flap 100. In FIG. 7C, the electric apparatus 30 has raised the front flap 100 and the contact electrodes 56 are in contact with the counter electrodes 110.

FIG. 1 also illustrates an embodiment where the electric apparatus 30 includes the bio-signal measurement device 20. FIG. 1 also illustrates an embodiment, where the bio-signal measurement device 20 is in wired connection with the electric apparatus 30, which in this embodiment is a wired connector.

In an embodiment, the front flap 100 comprises at least one mechanical coupling element 120 for a mechanical connection with a mechanical counterpart 120' of the electric apparatus 30. The at least one mechanical coupling element 120 may comprise a hole or a weakened area i.e. a preform of a hole, for example, for the coupling.

In an embodiment, the disposable patch electrode structure 10 further may comprise the first side flap 200 and the second side flap 202.

In embodiment, the first side flap 200 may be separated from the patch electrode structure 10 by a non-enclosing first side flap cut 102' which may be connected or included in the non-enclosing front flap cut 102. The first side flap cut 102' may be united with the front flap cut 102 and they may form a single flap cut unseparable from each other. Material of the first side flap 200 is thus formed as continuous material of the main structure 90 such that materialistic connection 206 of the continuous material between a rear section 204 of the first side flap 200 at a non-enclosing side of the first side flap cut 200 and the main structure 90 are configured to allow tilt of the first side flap 200 in a direction of a normal N of the main structure 90 with respect to the main structure 90. The tilt may be caused by a face 152 of the electric apparatus 30. The side flaps 200, 202 may have mechanical coupling elements 220, 222 similar to the mechanical coupling element 120 of the front flap 100 for their mechanical coupling counterpart elements 220', 222' of the electric apparatus 30.

The second side flap 202 may be separated from the patch electrode structure 10 by a non-enclosing second side flap cut 102", which may be connected or included in the non-enclosing front flap cut 102. The second side flap cut 102" may be united with the front flap cut 102 and or the first side flap cut 102' and they may form a single flap cut unseparable from each other. Material of the second side flap 202 is thus formed as continuous material of the main structure 90 such that materialistic connection 206' of the continuous material between a rear section 204' of the second side flap 202 at a non-enclosing side of the second side flap cut 202 and the main structure 90 is configured to allow tilt of the second side flap 202 with respect to the main structure 90.

The first side flap 200 and the second side flap 202 may face each other spaced by a predetermined gap therebetween when raised against the sides of the electric apparatus 30. The predetermined gap may be matched with the electric apparatus 30. The first side flap 200 and the second side flap 202 are configured to tilt in opposite directions with respect to each other based on the continuous materialistic connections 206, 206'. In addition to that, the first side flap 200 and the second side flap 202 are configured to tilt in a direction perpendicular to the tilt of the front flap 100 while the front flap 100, the first side flap 200 and the second side flap 202 rise to same direction parallel to the normal N of the main structure 90. That is, the front flap 100, the first side flap 200 and the second side flap 202 rise above the main structure 20 on the same side of the patch electrode structure 10.

The frontal section 108 of the front flap 100 may be configured to face to or reside within the gap between the first side flap 200 and the second side flap 202.

Figure 8:
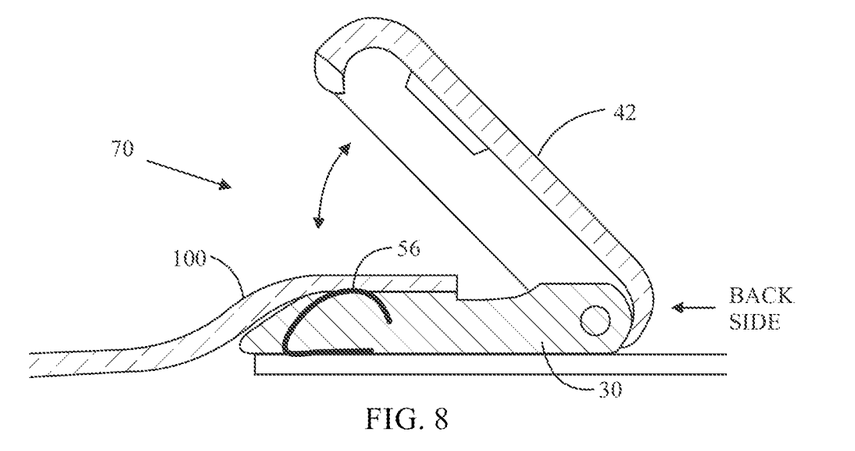
FIG. 8 illustrates an example of a lid and opening.

FIG. 8 illustrates an example of the lid 42 and the opening 70. When lid 42 is open, the front flap 100 can enter the volume of the electric apparatus 30 under the lid 42. After that the lid 42 can be closed for an efficient and proper mechanical and electrical contact between the electric apparatus 30 and the patch electrode structure 10.

Figure 9:
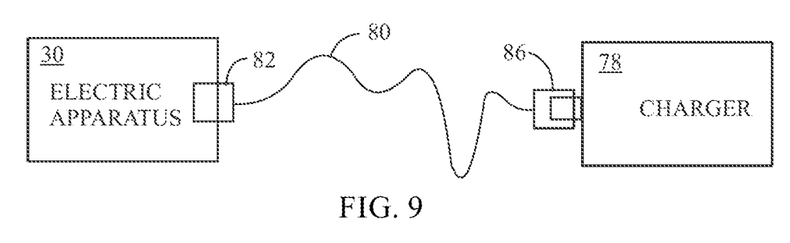
FIG. 9 illustrates an example of charging of the electric apparatus.

FIG. 9 illustrates an example where the electric apparatus 30 is connected with an electric charger 78 for charging a battery of the electric apparatus 30. Instead of charger 78, the electric apparatus 30 be electrically connected with other electric apparatuses such data processing and/or data storing apparatuses. Then instead of pure electric energy, measured information can be transferred from the electric apparatus 30. Additionally, data, commands and/or computer programs may be transferred.

The connection can be realized by opening the lid 42, removing a the front flap 100 or any other similar connector from the front part 42, inserting a first connector 82 of a wire 80 similar to the front flap 100 into the volume between the frame part 44 and the lid 42. After that the lid 42 can be closed for securing the electric and mechanical connection between the first connector 82 and the electric apparatus 30, the charging may begin if also a potential second connector 86 of the wire 80 is properly connected with the charger 78. Data transfer may be performed in a similar manner.

Figure 10:
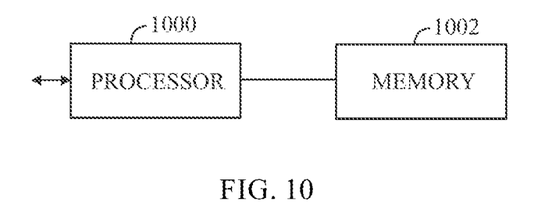
FIG. 10 illustrates an example of bio-signal measurement device that performs data processing.

FIG. 10 illustrates an example of the non-disposable bio-signal measurement device as the electric apparatus 30. The electric apparatus then comprises one or more processors 1000 and one or more memories 1002 including computer program code. The one or more memories 1002 and the computer program code may be configured to, with the one or more processors 1000, cause the electric apparatus 30 at least to receive bio-signal from the patch electrode structure 10 and perform data processing of the bio-signal.

Structurally, the electric apparatus 30 may be described in the following manner. The basic structure may comprise two separate main parts—housing, which includes the front part 40 (lid 42 and the frame part 44) and assembled PCB structure or the like, which includes the extension plate 54. The assembled PCB structure can be made to have a direct contact to the disposable patch electrode structure 10. Hence, no separate connectors are needed.

The housing and the assembled PCB structure are fixed together with sliding structure that forms a piled structure between the PCB structure and the housing.

The main assembly of the housing and the PCB are sealed up with lock part that snaps the PCB structure into the housing and pre-locks it in correct position.

The lock feature pre-locks the necessary parts in place and enables resin such as dispension glue to be added to the structure from purposely designed holes with cavities where air can be pushed out. No gaskets or screws are needed on device/adapter assembly. The resin makes the electric apparatus water and sweat proof while still having a simple and repeatedly openable and closable connection structure for the disposable patch electrode structure 10 and also for other devices such as charger 78, for example.

Figure 11:
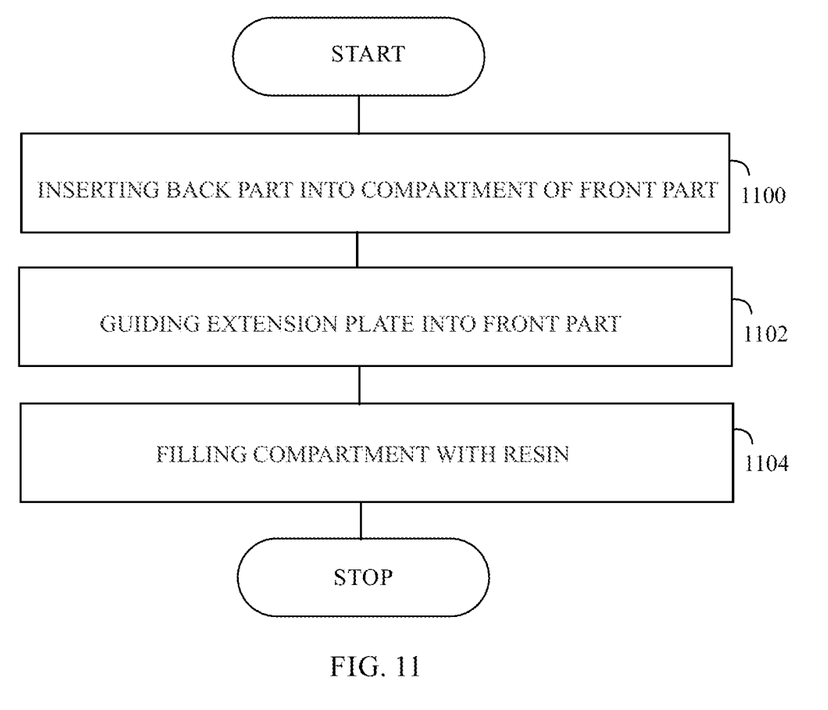
FIG. 11 illustrates of an example of a flow chart of a manufacturing method.

FIG. 11 is a flow chart of the manufacturing method of an electric apparatus of a bio-signal measurement system. In step 1100, a back part 50 is inserted into a compartment 46 of a front part 40 of the electric apparatus 30, the back part 50 comprising an electric circuit conductors 34 and an extension plate 54.

In step 1102, an extension plate 54, which comprises first electric contacts 56 of the electric circuit conductors 34, is guided into the front part 40 while inserting the back part 50 within the compartment 46, the first electric contacts 56 acting as counter-electrodes for electrodes 110 of a front flap 100 of a disposable patch electrode structure 10 and the electric apparatus 30 being configured receive the front flap 100 of the disposable patch electrode structure 10 into a volume of the front part 40 for a contact between the first electric contacts 56 and the electrodes 110 of the front flap 100.

In step 1104, the compartment 46 is filled with resin received through the resin holes 58 which are part of at least one of the back part 50 and the front part 40, the resin being configured immobilize the front part 40 and the back part 50 with respect to each other and attaching them together.

It will be obvious to a person skilled in the art that, as technology advances, the inventive concept can be implemented in various ways. The invention and its embodiments are not limited to the example embodiments described above but may vary within the scope of the claims.

What is claimed is:

1. An electric apparatus of a bio-signal measurement system, the electric apparatus comprising:
a front part and a back part; wherein:
the electric apparatus is non-disposable;
the front part comprises a compartment at a back side of the front part, the compartment being configured to house the back part when inserted therein;
the back part comprises electric circuit conductors and an extension plate, which is configured to extend to the front part within the electric apparatus;
the extension plate comprises first electric contacts of the electric circuit conductors, the first electric contacts being configured to reside within the front part when the back part is within the compartment, the first electric contacts acting as counter-electrodes for electrodes of a front flap of a disposable patch electrode structure;
the electric apparatus is configured receive the front flap of the disposable patch electrode structure into a volume of the front part to form a contact between the first electric contacts and the electrodes of the front flap;
at least one of the back part and the front part comprises resin holes, and the compartment contains resin received through the resin holes, the resin being configured to fill the compartment, make the electric apparatus water and sweat proof, and immobilize the front part and the back part with respect to each other and to attach them together;
the electric apparatus is configured to receive the front flap with the electrodes through an opening of a front part of a lid into a volume under the lid of the front part to form a contact between the first electric contacts and the electrodes of the front flap, and
the opening, under the lid, is configured to receive side flaps at both sides of electric apparatus, and the lid is configured to cause pressure between the sides and the side flaps while the lid is closed for securing a mechanical contact between the electric apparatus and the disposable patch electrode structure.

2. The electric apparatus of claim 1, wherein the front part comprises a wall at an end of the compartment within the front part, the wall comprising an aperture;
the extension plate is configured to extend through the aperture, shapes of the aperture and the extension plate being matched together; and
the first electric contacts being configured to reside within the front part when the extension plate has penetrated the aperture while the back part is within the compartment.

3. The electric apparatus of claim 1, wherein a wall is configured to keep a volume of the front part within which the first electric contacts reside and the compartment as separate departments and prevent the resin from entering the volume of the front part.

4. The electric apparatus of claim 1, wherein the front part comprises the lid and a frame part, the frame part and the lid together comprising or being mechanically connected with a quick locking mechanism configured to lock the lid in the closed position with respect to the frame part, the lid being configured to open at a face of the front part to form an opening to the front part.

5. The electric apparatus of claim 1, wherein the electric apparatus is configured to slide on a main structure of the disposable patch electrode structure toward the front flap of the patch electrode structure with the face ahead, and
the lid is configured to cause pressure between the first electric contacts and the electrodes of the front flap while the lid is closed.

6. The electric apparatus of claim 1, wherein the front part and the back part together comprise a non-openable instant interlocking structure which is configured to attach the front part and the back part together and prevent them from moving with respect to each other.

7. A method of manufacturing an electric apparatus of a bio-signal measurement system, the method comprising:
inserting a back part of the electric apparatus into a compartment of a front part of the electric apparatus, the back part comprising electric circuit conductors and an extension plate;
guiding the extension plate, which comprises first electric contacts of the electric circuit conductors, into the front part while inserting the back part within the compartment, the first electric contacts acting as counter-electrodes for electrodes of a front flap of a disposable patch electrode structure and the electric apparatus being configured receive the front flap of the disposable patch electrode structure into a volume of the front part for a contact between the first electric contacts and the electrodes of the front flap; and
filling the compartment with resin received through the resin holes which are part of at least one of the back part and the front part, the resin being configured to fill the compartment, make the electric apparatus water and sweat proof, and immobilize the front part and the back part with respect to each other and to attach them together, wherein the electric apparatus is non-disposable, wherein the electric apparatus is configured to receive the front flap with the electrodes through an opening of a front part of a lid into a volume under the lid of the front part to form a contact between the first electric contacts and the electrodes of the front flap, and wherein the opening, under the lid, is configured to receive side flaps at both sides of electric apparatus, and the lid is configured to cause pressure between the sides and the side flaps while the lid is closed for securing a mechanical contact between the electric apparatus and the disposable patch electrode structure.

8. The method of claim 7, wherein the front part comprises a wall at an end of the compartment within the front part, the wall comprising an aperture;

the extension plate is configured to extend through the aperture, shapes of the aperture and the extension plate being matched together; and the first electric contacts being configured to reside within the front part when the extension plate has penetrated the aperture while the back part is within the compartment.

9. The method of claim 7, wherein a wall is configured to keep a volume of the front part within which the first electric contacts reside and the compartment as separate departments and prevent the resin from entering the volume of the front part.

10. The method of claim 7, wherein the front part comprises the lid and a frame part, the frame part and the lid together comprising or being mechanically connected with a quick locking mechanism configured to lock the lid in the closed position with respect to the frame part, the lid being configured to open at a face of the front part to form an opening to the front part.

11. The method of claim 7, wherein the electric apparatus is configured to slide on a main structure of the disposable patch electrode structure toward the front flap of the patch electrode structure with the face ahead, and the lid is configured to cause pressure between the first electric contacts and the electrodes of the front flap while the lid is closed.

12. The method of claim 7, wherein the front part and the back part together comprise a non-openable instant interlocking structure which is configured to attach the front part and the back part together and prevent them from moving with respect to each other.

* * * * *